United States Patent [19]

Baille-Barrelle et al.

[11] 4,185,114
[45] Jan. 22, 1980

[54] SULFUR-CONTAINING N-BENZYLAMINO-ACIDS AND SALTS THEREOF

[75] Inventors: Henri Baille-Barrelle, La Chapelle en Serval; Maurice Vigneron, Paris; Charles Lespagnol, Lambersart, all of France

[73] Assignee: Boehringer Ingelheim GmbH, Ingelheim am Rhine, Fed. Rep. of Germany

[21] Appl. No.: 810,087

[22] Filed: Jun. 27, 1977

[30] Foreign Application Priority Data

Jun. 28, 1976 [DE] Fed. Rep. of Germany ....... 2628911

[51] Int. Cl.$^2$ ................. C07C 153/09; C07C 149/43; A61K 31/235; A61K 31/195
[52] U.S. Cl. ................................ 424/301; 424/309; 424/319; 560/16; 562/426; 260/455 R
[58] Field of Search ............ 560/16; 260/516, 455 R; 424/309, 301, 319; 562/426

[56] References Cited

U.S. PATENT DOCUMENTS

| 3,177,222 | 4/1965 | Surrey .................................. 260/516 |
| 3,950,542 | 4/1976 | Kalopissis ............................. 424/316 |

Primary Examiner—James O. Thomas, Jr.
Assistant Examiner—Michael Shippen
Attorney, Agent, or Firm—Hammond & Littell

[57] ABSTRACT

Compounds of the formula

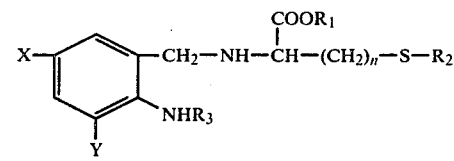

wherein
X and Y, which may be identical to or different from each other, are each hydrogen or halogen,
$R_1$ is hydrogen or straight or branched alkyl of 1 to 4 carbon atoms,
$R_2$ is hydrogen, straight or branched alkyl of 1 to 3 carbon atoms, carboxy-lower alkyl or acyl, preferably lower aliphatic carboxylic acyl,
$R_3$ is hydrogen or acyl, preferably lower aliphatic carboxylic acyl, and
n is 1 or 2;

non-toxic, pharmacologically acceptable acid addition salts thereof; sulfonium salts thereof; and, when $R_1$ is hydrogen, salts thereof formed with inorganic or organic bases or basic aminoacids. The compounds as well as their various salts are useful as mucolytics.

12 Claims, No Drawings

SULFUR-CONTAINING N-BENZYLAMINO-ACIDS AND SALTS THEREOF

This invention relates to novel sulfur-containing carboxylic N-benzylamino-acids and salts thereof, as well as to various methods of preparing these compounds.

More particularly, the present invention relates to a novel class of compounds represented by the formula

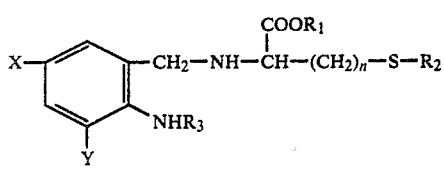

wherein
X and Y, which may be identical to or different from each other, are each hydrogen or halogen,
$R_1$ is hydrogen or straight or branched alkyl of 1 to 4 carbon atoms,
$R_2$ is hydrogen, straight or branched alkyl of 1 to 3 carbon atoms, carboxy-lower alkyl or acyl, preferably lower aliphatic carboxylic acyl,
$R_3$ is hydrogen or acyl, preferably lower aliphatic carboxylic acyl, and
n is 1 or 2;
non-toxic, pharmacologically acceptable acid addition salts thereof; sulfonium salts thereof; and, where $R_1$ is hydrogen, salts thereof formed with inorganic or organic bases or basic aminoacids.

A preferred sub-genus thereunder is constituted by compounds of the formula I, wherein
X and Y are each hydrogen or bromine,
$R_1$ is hydrogen, methyl or ethyl,
$R_2$ is methyl, carboxymethyl or lower alkanoyl,
$R_3$ is hydrogen, and
n is 1 or 2;
non-toxic, pharmacologically acceptable acid addition salts thereof formed with inorganic or organic acids, such as hydrochloric acid, hydrobromic acid, sulfuric acid, phosphoric acid, lactic acid, citric acid, tartaric acid, maleic acid, pamoic acid, decylic acid, theophylline-sulfonic acid or theophylline-acetic acid; sulfonium salts thereof wherein the sulfur is bonded to a methyl or ethyl substituent on the one hand and to a bromine or chlorine atom on the other hand, as well as to the substituent $R_2$; and, when $R_1$ is hydrogen, salts thereof formed with a basic aminoacid selected from the group consisting of lysine, arginine, histidine and or nithine.

An especially preferred sub-genus is constituted by compounds of the formula I, wherein
X and Y are each hydrogen or bromine,
$R_1$ is hydrogen,
$R_2$ is methyl or carboxymethyl,
$R_3$ is hydrogen, and
n is 1 or 2.

The compounds embraced by formula I may be prepared by a process which comprises the following steps:
(a) Preparation of an N-(2-nitro)-benzylated derivative of the formula

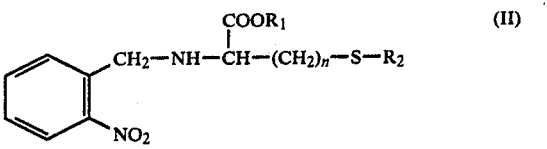

wherein $R_1$, and $R_2$ and n have the same meanings as in formula I;
(b) Reduction of the nitro group to the amino group;
(c) Optional halogenation of the (2-amino)-benzylated derivative obtained in b>, and/or
(d) Optional acylation of the amino group in the 2-position of the benzyl group; and/or
(e) Optional addition reaction with an inorganic or organic acid, an inorganic or organic base or a basic amino acid, or production of a sulfonium derivative by conventional alkylation.

The starting compounds of the formula II are obtained by condensation between an o-nitrobenzaldehyde and an aminated compound of the formula

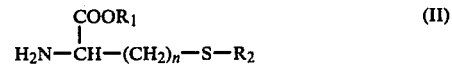

where n, $R_1$ and $R_2$ have the meanings defined in formula I, and subsequent direct reduction in the reaction medium of the resulting Schiff's base of the formula

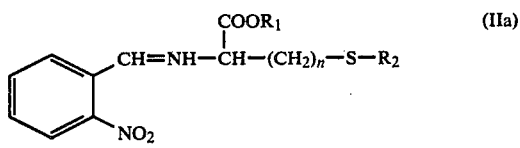

where n, $R_1$ and $R_2$ have the meanings defined above (which does not need to be isolated).

The compounds of the formula I, where X, Y and $R_3$ are each hydrogen, are obtained by reduction of the corresponding compound of the formula II with molecular hydrogen in the presence of a hydrogenation catalyst.

The compounds of the formula I, when X and/or Y are chlorine or bromine, are prepared by halogenating the corresponding compound obtained in step (b) according to the conventional process for nuclear halogenation.

The compounds of the formula I, where $R_3$ is acyl, are obtained by reacting the corresponding derivative obtained in step (b) or (c), where $R_3$ is hydrogen, with a corresponding acylating compound, such as acetyl chloride, acetic acid anhydride, or the like.

The addition salts with inorganic or organic acids, with inorganic or organic bases or basic aminoacids of the compounds according to the invention are prepared by reacting the corresponding compounds of the formula I with the desired acid, the special base or the desired aminoacid under conventional conditions. The sulfonium salts are also prepared by conventional methods, for example, by alkylation with an alkyl halide.

The compounds embraced by formula I may also be prepared by a process comprising the following steps:
(a) Condensation of a derivative of a 2-aminobenzyl alcohol of the formula

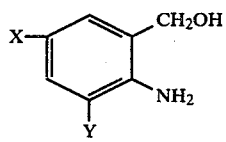

where X and Y have the meanings defined above, in the presence of an acid, such as mainly acetic acid, propionic acid, n-butyric acid, isobutyric acid, valeric acid, isovaleric acid, trimethylacetic acid, caproic acid or capric acid, or (b) of a benzyl alcohol derivative of the formula

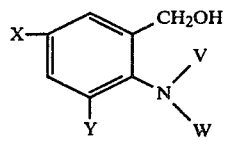

where

X and Y have the meanings defined above,

V is hydrogen or acyl, preferably acetyl, and

W is acyl, preferably acetyl, with an aminated compound of the formula III.

The compounds of the formula I may also be prepared by the following process; Reacting a diacylaminobenzyl halide of the formula

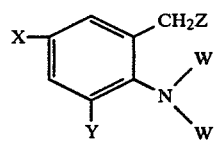

where W, X and Y have the above-mentioned meanings, and Z is chlorine or bromine, with a compound of the formula III, and subsequently removing of the acyl groups, for example by heating with a dilute mineral acid or a base. This reaction is preferably effected in the presence of binding agent for hydrohalic acids.

Suitable binding agents for hydrohalic acids are tertiary inorganic or organic bases or an excess of the compound of the formula III (at least one mol excess). It is of advantage to use an inert organic solvent, such as methanol, benzene or toluene.

The compounds of the formula II, as well as the compounds of the formula IIa are novel, useful intermediates for the preparation of compounds of the formula I.

The following examples illustrate the present invention and will enable others skilled in the art to understand it more completely. It should be understood, however, that the invention is not limited solely to the particular examples given below.

EXAMPLE 1

N-(2-Amino-benzyl)-methionine (a) 500 gm of methionine and 560 gm of o-nitro-benzaldehyde were gradually added to a sodium hydroxide solution which was prepared by dissolving 134 gm of sodium hydroxide in tablet form in 3.5 liters of water. The resulting mixture was stirred first for one hour at room temperature and then for two hours at 30°–35° C. Thereafter, the reaction mixture was cooled to 15° C., and a total 57 gm of sodium borohydride was added in small portions while maintaining the temperature at about 15° C. Subsequently, the reaction mixture was allowed to stand overnight, it was then washed with ether, and the aqueous phase was separated and adjusted to pH3 with hydrochloric acid. The precipitate formed thereby was centrifuged off, washed with a little water and dried at 60° C. in a ventilated drying chamber. 800 gm (84% of theory, based on the methionine reactant) of yellow crystalline N-(2-nitro-benzyl)-methionine, m.p. 180° C., of the formula

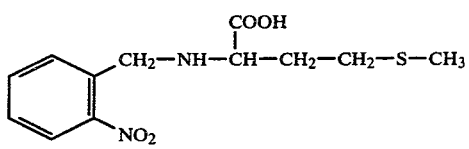

were obtained.

(b) 780 gm of N-(2-nitro-benzyl)-methionine were dissolved in a mixture of 5 liters of methanol and 280 cc of aqueous 30% sodium hydroxide in a tightly sealable vessel equipped with an effective stirrer. 100 gm of Raney nickel were added to the solution, the vessel was sealed, and the contents were hydrogenated at a pressure of about 70 gm/cm$^2$, accompanied by stirring. The internal temperature rose gradually to about 60° C. and fell again when the hydrogenation reaction had gone to completion. The reaction mixture was then cooled to room temperature, the Raney nickel was filtered off, and the methanolic filtrate was neutralized with acetic acid, whereupon the hydrogenated product slowly precipitated out. The reaction mixture was allowed to stand overnight. The precipitated substance was centrifuged off, washed with a little methanol, and dried at 60° C. in a ventilated drying chamber, yielding 570 gm (80% of theory) of the creme-colored crystalline compound of the formula

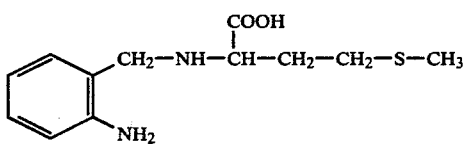

which had a melting point of 217° C.

EXAMPLE 2

N-(2-Amino-5-bromo-benzyl)-methionine 2.54 gm (0.01 mol) of N-(2-amino-benzyl)-methionine and 100 gm of aluminum chloride were dissolved in 50 cc of anhydrous acetic acid while gently heating. Then, the mixture was brought to room temperature and, while stirring, 0.52 cc (0.01 mol) of bromine diluted in 20 cc of acetic acid was added slowly. A light-colored precipitate was formed. After the addition of bromine was finished, the precipitate was centrifuged off, washed with ample acetic acid and then with anhydrous ether, and dried in a dryer. Then, the product was dissolved in 40 cc of water, and the pH of the solution was adjusted to 6 by addition of dilute ammonia while cooling it on an ice water bath. The mixture was allowed to stand for 24 hours, whereupon the new precipitate was centrifuged off, washed with water and dried in drying chamber. (Solvent of the crystallizate: alcohol at 50°

C.). The melting point of the product was 207° C., and the yield was 45% of theory.

EXAMPLE 3

N-(2-amino-3.5-dibromo-benzyl)-methionine 90 gm of N-(2-amino-benzyl)-methionine were dissolved in 9 liters of acetic acid at a temperature of 60° to 65° C. After addition of 9 gm of iron powder, a solution of 45 cc of bromine in 500 cc of acetic acid was introduced while maintaining a temperature of 62° to 65° C. After the introduction of bromine was finished, stirring was continued for 15 minutes, and then the acetic acid was removed by distillation under reduced pressure up to dryness. A thick oil was obtained, to which 500 gm of shaved ice and a solution of 300 cc of 30% sodium carbonate in 1.8 liters of water were consecutively added. The mixture was stirred for half an hour, the iron hydroxide which had formed was filtered off, and the filtrate was neutralized with hydrochloric acid. Raw N-(2-amino-3.5-dibromo-benzyl)-methionine precipitated out in the form of large orange-colored crystals. These crystals were centrifuged off, washed with water and dried in a ventilated drying chamber at 60° C. yielding 150 gm of the crude product (quantitative yield).

The raw product was purified by chromatography on silica-gel (3 kg; for elution a mixture of chloroform/methanol/ammonia: 80/15/5 was used). The fraction containing the N-(2-amino-3.5-dibromo-benzyl)-methionine yielded, after neutralization with acetic acid, 40 gm of the pure product (yield: 27.5% of theory; melting point 209° C.).

EXAMPLE 4

N-(2-Amino-3.5-dibromo-benzyl)-methionine chlorohydrate 150 gm of N-(2-amino-3.5-dibromo-benzyl)-methionine were suspended in 650 ml of isopropyl alcohol. While stirring, the suspension was heated to 80° C. and, while stirring was continued, about 30 ml of hydrochloric acid of 1.18 density were added, so that a solution of pH 1 was obtained. A liquefaction was observed, followed by immediate formation of a precipitate. While stirring was continued, the precipitate was centrifuged off and washed with 80 ml of ice-cold isopropyl alcohol. After drying at 60° C. in a ventilated drying chamber, 147 gm of the desired product were obtained in the form of white crystals, which melted at 212° C.

EXAMPLE 5

N-(2-amino-3.5-dibromo-benzyl)-methionine maleate 100 gm of N-(2-amino-3.5-dibromo-benzyl)-methionine were dissolved in 500 ml of hot acetic acid, and then, while stirring and heating the solution at the boiling point, 28 gm of maleic acid were added. After it had dissolved, the solution was cooled to 20° C. while stirring was continued, and the precipitated product was centrifuged off, washed with a little acetic acid and then with isopropylic acid, and after drying at 60° C. in a ventilated drying chamber, 107 gm of the desired product were obtained in the form of white crystals, which melted at 205° C.

EXAMPLE 6

N-(2-amino-benzyl)-S-methyl-cysteine (a) N-(2-nitro-benzyl)-S-methyl-cysteine was prepared in analogy to Example 1(a), by reacting S-methyl-cysteine via o-nitrobenzaldehyde in the presence of sodium hydroxide solution and subsequent reduction of the Schiff's base which was obtained with sodium borohydride. Melting point: 155° C.

(b) N-(2-amino-benzyl)-S-methyl-cysteine of the formula

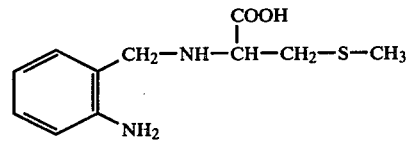

was prepared in analogy to Example 1 (b) by reducing N-(2-nitro-benzyl)-S-methyl-cysteine with hydrogen under pressure in the presence of sodium carbonate and Raney nickel. Melting point: 193° C.

EXAMPLE 7

N-(2-amino-5-bromo-benzyl)-S-methyl-cysteine

To a stirred suspension of 2.40 gm of N-(2-amino-benzyl)-S-methyl-cysteine in 50 cm³ anhydrous methanol a solution of 0.52 cc of bromine in 20 cc of methanol was added dropwise. After the addition of bromine was finished, stirring was continued for 2 hours. The solvent was evaporated in vacuo on a water bath, and residue was dissolved in 50 cc of distilled water. The aqueous solution was decolored by refluxing for 1 hour in the presence of a small quantity of charcoal. The coal was removed by filtration, and the pH of the filtrate was adjusted to 5 by addition of dilute ammonia. The desired product precipitated out. The mixture was allowed to stand for several hours, whereupon the precipitate was centrifuged off, washed with water and dried in a drying chamber. Melting point: 228° C.

EXAMPLE 8

N-(2-amino-3.5-dibromo-benzyl)-S-methyl-cysteine was prepared in analogy to Example 3, by reacting bromine with N-(2-amino-benzyl)-S-methyl-cysteine. Melting point: 240° C.

EXAMPLE 9

N-(2-amino-benzyl)-S-carboxymethyl-cysteine (a) N-(2-nitro-benzyl)-S-carboxymethyl-cysteine, m.p. 177° C., was prepared in analogy to Example 1 (a), by reacting S-carboxymethyl-cysteine with o-nitro-benzaldehyde in the presence of sodium hydroxide solution, and subsequent reduction of the Schiff's base with sodium borohydride.

(b) N-(2-amino-benzyl)-S-carboxymethyl-cysteine was prepared in analogy to Example 1 (b) by reducing N-(2-nitro-benzyl)-S-carboxymethyl-cysteine with hydrogen in the presence of Raney nickel and double the quantity of soda. Melting point: 214° C.

EXAMPLE 10

Lysine Salt of N-(2-amino-3.5-dibromobenzyl)-methionine

A mixture of 1.46 gm (0.01 mol) of L(+)-lysine base, 4.12 gm (0.01 mol) of N-(2-amino-3.5-dibromo-benzyl)-methionine and 200 cc of 80% methanol was refluxed. The resulting hot solution was filtered in order to remove insoluble particles.

The filtrate was evaporated under reduced pressure, the residue was taken up twice in 10 cc absolute alcohol, and the solution was evaporated to dryness. The resulting crystals were dried in vacuo. 5.3 gm of the hygroscopic salt without a distinct melting point (yield 95% of theory) were obtained. Decomposition occurred and the product became pasty at 100° C. It was soluble in water and alcohol.

The compounds of the present invention, that is, those embraced by formula I and their salts, have useful pharmacodynamic properties. More particularly, they exhibit mucolytic activity in warm-blooded aminals, such as guinea pigs, and are therefore useful for the treatment of hypersecretions of the bronchia.

One of the compounds according to the invention, namely N-(2-amino-3.5-dibromo-benzyl)-methionine (compound A), was compared with known mucolytic compounds, namely S-carboxymethyl-cysteine (SCMC) and N-[2-amino-2.5-dibromo-benzyl]-N-methyl-cyclohexylamino-chlorohydrate (bromhexine), in regard to their effect upon bronchial hypersecretion provoked by irritation.

Guinea pigs which had inhaled on 3 consecutive days ammonia vapors delivered by an atomizer in a fixed and controlled quantity, were treated with the test compounds and, immediately after the last inhalation of ammonia vapor, were observed for one week.

After sacrificing the animals, removing of the lungs, fixing of the tissue, paraffin slide, staining by the trichrome method of Masson (hematoxylene-Fuchsin-Ponceau and aniline blue) and by P.A.S. Bleu Alcian (special staining of the muco-polysaccharides), the determination of the histological section of the lung parenchyma was made in a "blind" way. Thus, the various activities of the test compounds could be proved, that is proved by comparison with the observations made on guinea pigs which had inhaled ammonia vapor but had remained untreated. A statistical study was made according to the non-parametric test of Mann-Whitney (see S. Siegel in "Non-parametric statistics for the behavioral Science" (1956) page 116—Intern. Student Edition—McGraw-Hill Book Co., Inc.).

The complete study was made with 174 male guinea pigs, which were tri-colored and weighted between 350 and 450 gm; it was carried out in 2 blocks of experiments, each of the blocks comprised, besides treated animals, three healthy guinea pigs and 12 "NH$_3$-sick" guinea pigs.

The statistical studies made with the results of the P.A.S. Bleu Alcian-staining, are shown in the following tables:

Table I

| effected comparisons (quantities in mg/kg) | B + M + A* | | A** | | S** | |
|---|---|---|---|---|---|---|
| | a | b | a | b | a | b |
| compound A 468.7 | 1.71 | | 0.71 | | 0.38 | |
| | | NS | | NS | | NS |
| Bromohexine 468.7 | 2.29 | | 1.29 | | 0.79 | |
| compound A 187.5 | 1.79 | | 0.63 | | 0.67 | |
| | | 0.02 | | 0.002 | | NS |
| SCMS 468.7 | 3.71 | | 1.50 | | 1.13 | |
| compound A 468.7 | 1.71 | | 0.71 | | 0.38 | |
| | | 0.10 | | NS | | 0.002 |

Table I-continued

| effected comparisons (quantities in mg/kg) | B + M + A* | | A** | | S** | |
|---|---|---|---|---|---|---|
| | a | b | a | b | a | b |
| SCMC 937.4 | 2.92 | | 1.13 | | 1.25 | |

\* = quantity of cell mucus in the lower, middle and upper range
\*\* = mucus in the upper range
\*\*\* = secreted mucus
a = middle index: the lower it is, the more active is the product
b = probability (work hypothesis: Is there a difference in activity among the products concerned?)
NS = P>0,10

Table II

| effected comparisons (quantity in mg/kg) | B + M + A* | | A** | | S*** | |
|---|---|---|---|---|---|---|
| | a | b | a | b | a | b |
| compound A 468.7 | 0.67 | | 0.13 | | 0.17 | |
| | | NS | | NS | | NS |
| Bromhexine 468.7 | 1.17 | | 0.46 | | 0.17 | |
| compound A 187.5 | 0.88 | | 0.42 | | 0.17 | |
| | | 0.05 | | 0.02 | | 0.05 |
| SCMC 468:7 | 2.21 | | 0.83 | | 0.67 | |
| compound A 468.7 | 0.67 | | 0:13 | | 0.17 | |
| | | 0.02 | | 0.002 | | NS |
| SCMC 937.4 | 1.71 | | 0.83 | | 0.25 | |

Table III

| effected comparisons (quantities in mg/kg) | B + M + A* | A** | S*** |
|---|---|---|---|
| compound A 468.7 | 2.38 | 0.83 | 0.54 |
| | NS | 0.10 | NS |
| Bromohexine 468.7 | 3.46 | 1.75 | 0.96 |
| compound A 187.5 | 2.67 | 1.04 | 1.08 |
| | 0.02 | 0.002 | 0.10 |
| SCMC 468.7 | 5.79 | 2.46 | 1.79 |
| compound A 468.7 | 2.38 | 0.83 | 0.54 |
| | 0.02 | 0.002 | 0.02 |
| SCMC 937.4 | 4.63 | 1.96 | 1.50 |

An examination of the results shown in Tables I, II and III makes it possible to estimate the action of the products upon the mucous secretion, as disclosed in the histological sections by the P.A.S. Bleu Alcian-staining. This mucous secretion is indicated, above all, on account of the significance of the mucus in the upper range of the cup-shaped cells and by the significance of the secreted mucus for the bronchial branches.

If the quantity of the neutral mucopolysaccharides, stained with the P.A.S. Bleu Alcian in the range of the epithelial cells of the bronchi and bronchioles, is examined for the first time, the compounds may be arranged in the following sequence for the dose 468.7 mg/kg (Table III): Compound A, bromhexine, S.C.M.C.

For the secretion of mucus in the bronchial branches (Table I) the same classification is valid.

The indications made in Tables I, II and III show that—though there is no statistically significant difference between bromhexine and compound A at the dose of 468.7 mg/kg for the mucus in the range of the large bronchi and the bronchioles—the average indices are always weaker at 468.7 mg/kg with compound A and that the level of probability of 0.10 in favor of compound A is reached, when considering the mucus in the upper range of the total "large bronchi and bronchioles".

Above all, these statistical comparisons show the superiority of compound A over the S.C.M.C., with a weak dose for the two compounds (be it with 187.5 mg/kg of compound A for 468.7 mg/kg of compound A for 937.4 mg/kg of S.C.M.C.); this fact is visible in the range of the large bronchi and in the bronchioles, or in the total range "large bronchi and bronchioles".

Conclusions from the Pharmacological Study

The repeated inhalation of ammonia vapors provokes in the guinea pig a significant relative secretion of mucus, especially in the epithelial range of the large bronchi and the bronchioles. Compound A distinctly reduces this secretion and in a more striking manner than the comparative compounds.

Toxicity

The study of toxicity was effected in male, tri-colored guinea pigs weighing 400 gm each. The animals received 8 consecutive doses at 24-hour intervals, of a dispersive agent (aqueous solution of carboxymethyl cellulose, enriched up to 0.25% with Tween 80—wetting agent—in the ratio of 0.2%) to which the studies test compound was added in the ratio of 1200 mg/kg.

The tests were effected with N-(2-amino-benzyl)-methionine as well as with N-(2-amino-3.5-dibromo-benzyl)-methionine; no animal died during the time of observation. It may be concluded therefrom that the products according to the invention are not toxic at conventional dosage levels.

The compounds according to the invention are useful mainly for the treatment of hypersecretory disorders of the bronchi as well as for the treatment of hypersecretory disorders characteristic of the presence of viscous mucus, the natural excretion of which is difficult.

Therefore, the compounds according to the invention may be used for the treatment of strong and chronic bronchitis, bronchorrhea, bronchiectasis, emphysema of the lung, asthma and all diseases which provoke a pathologic secretion.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective mucolytic dosage unit of the compounds according to the present invention is from 0.33 to 1.34 mgm/kg body weight.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

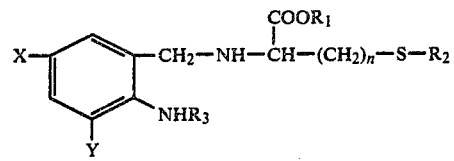

wherein
X and Y are each hydrogen or halogen,
$R_1$ is hydrogen or alkyl of 1 to 4 carbon atoms,
$R_2$ is hydrogen, alkyl of 1 to 3 carbon atoms, carboxy-lower alkyl or lower aliphatic carboxylic acyl,
$R_3$ is hydrogen or lower aliphatic carboxylic acyl, and
n is 1 or 2;
a non-toxic, pharmacologically acceptable acid addition salt thereof; or, when $R_1$ is hydrogen, a non-toxic, pharmacologically acceptable salt thereof formed with an inorganic or organic base.

2. A compound of claim 1, where
X and Y are each hydrogen or bromine,
$R_1$ is hydrogen, methyl or ethyl,
$R_2$ is methyl, carboxymethyl or acetyl,
$R_3$ is hydrogen, and
n is 1 or 2.

3. A compound of claim 1, where
X and Y are each hydrogen or bromine,
$R_1$ is hydrogen,
$R_2$ is methyl or carboxymethyl,
$R_3$ is hydrogen, and
n is 1 or 2.

4. The compound of claim 1 which is N-(2-amino-benzyl)-methionine.

5. The compound of claim 1 which is N-(2-amino-5-bromo-benzyl)-methionine.

6. The compound of claim 1 which is N-(2-amino-3.5-dibromo-benzyl)-methionine.

7. The compound of claim 1 which is N-(2-amino-benzyl)-S-methyl-cysteine.

8. The compound of claim 1 which is N-(2-amino-5-bromo-benzyl)-S-methyl-cysteine.

9. The compound of claim 1 which is N-(2-amino-3.5-dibromo-benzyl)-S-methyl-cysteine.

10. The compound of claim 1 which is N-(2-amino-benzyl)-S-carboxymethyl-cysteine.

11. A mucolytic pharmaceutical dosage unit composition consisting essentially of an inert pharmaceutical carrier and an effective mucolytic amount of a compound of claim 1.

12. The method of destroying or dissolving excess mucus in the bronchia of a warm-blooded animal, which comprises perorally or parenterally administering to said animal an effective mucolytic amount of a compound of claim 1.